United States Patent [19]

Timmler et al.

[11] 4,400,388
[45] Aug. 23, 1983

[54] FUNGICIDAL 1-PHENYL-2-(1,2,4-TRIAZOL-1-YL)-ETHYL ETHERS

[75] Inventors: Helmut Timmler; Karl H. Büchel, both of Wuppertal; Wilhelm Brandes, Cologne; Paul-Ernst Frohberger; Hans Scheinpflug, both of Leverkusen, all of Fed. Rep. of Germany

[73] Assignee: Bayer Aktiengesellschaft, Leverkusen, Fed. Rep. of Germany

[21] Appl. No.: 43,070

[22] Filed: May 29, 1979

Related U.S. Application Data

[63] Continuation-in-part of Ser. No. 729,935, Oct. 6, 1976, Pat. No. 4,327,104.

[30] Foreign Application Priority Data

Oct. 27, 1975 [DE] Fed. Rep. of Germany ....... 2547953

[51] Int. Cl.³ ................... A01N 43/64; C07D 249/08
[52] U.S. Cl. .................................... 424/269; 424/232; 542/413; 548/262
[58] Field of Search .................... 260/308 R; 424/269, 424/232; 548/262

[56] References Cited

U.S. PATENT DOCUMENTS 3,717,655  2/1973  Godefroi et al. ................... 548/341

FOREIGN PATENT DOCUMENTS 2640823  3/1977  Fed. Rep. of Germany ... 260/308 R
2547953  4/1977  Fed. Rep. of Germany ...... 548/262

Primary Examiner—Alton D. Rollins
Attorney, Agent, or Firm—Sprung, Horn, Kramer & Woods

[57] ABSTRACT

1-Phenyl-2-(1,2,4-triazol-1-yl)-ethyl ethers of the formula

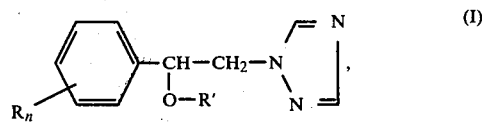

in which
R is halogen, alkyl, alkoxy, alkylthio, alkylsulfonyl, halogenoalkyl, nitro, cyano, optionally substituted phenyl or optionally substituted phenoxy,
R' is alkyl, alkenyl, alkynyl, optionally substituted phenyl, optionally substituted benzyl or optionally substituted styryl, and n is 0, 1, 2 or 3, and their salts, which possess fungicidal and bactericidal properties.

4 Claims, No Drawings

FUNGICIDAL 1-PHENYL-2-(1,2,4-TRIAZOL-1-YL)-ETHYL ETHERS

This is a continuation-in-part of Application Ser. No. 729,935, filed Oct. 6, 1976, now U.S. Pat. No. 4,327,104.

The present invention relates to and has for its objects the provision of particular new substituted 1-phenyl-2-(1,2,4-triazol-1-yl)-ethyl ethers which possess fungicidal and bactericidal properties, active compositions in the form of mixtures of such compounds with solid and liquid dispersible carrier vehicles, and methods for producing such compounds and for using such compounds in a new way especially for combating pests, e.g. fungi and bacteria, with other and further objects becoming apparent from a study of the within specification and accompanying examples.

It has been disclosed in German Published DOS No. 2,063,857 that 1-[β-aryl-β-(alkoxy)-ethyl]-imidazoles, such as, for example, 1-[β-butoxy-β-(4'-chlorophenyl)-ethyl]-imidazole (Compound A), exhibit a good fungicidal activity. However, in certain applications their action is not always entirely satisfactory, especially if low amounts and low concentrations are used. Furthermore, it is known from Phytopathology 33, 1113 (1063) that zinc ethylene-1,2-bis-dithiocarbamate (Compound B) is a good agent for combating fungal diseases of plants. However, its use as a seed dressing is only possible with limitations, since it is of low activity if low amounts and low concentrations are used.

The present invention now provides, as new compounds, the 1-phenyl-2-triazolyl-ethyl ether derivatives of the general formula

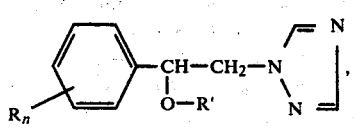

in which
R is halogen, alkyl, alkoxy, alkylthio, alkylsulfonyl, halogenoalkyl, nitro, cyano, optionally substituted phenyl or optionally substituted phenoxy,
R' is alkyl, alkenyl, alkynyl, optionally substituted phenyl, optionally substituted benzyl or optionally substituted styryl, and
n is 0, 1, 2 or 3,
and their salts.

Preferably, R represents halogen (especially fluorine, chlorine or bromine), nitro, cyano, alkyl or alkylsulfonyl, each with 1 to 4 carbon atoms, alkoxy or alkylthio, each with 1 or 2 carbon atoms, halogenoalkyl with up to 4 carbon atoms and up to 5 halogen atoms (especially with up to 2 carbon atoms and up to 3 identical or different halogen atoms, preferred halogens being fluorine and chlorine, as in, for example, trifluoromethyl), phenyl or phenoxy, the two last-mentioned radicals optionally carrying one or more substituents selected from halogen (especially fluorine, chlorine, and bromine), cyano, nitro and halogenoalkyl with 1 or 2 carbon atoms and up to 3 identical or different halogen atoms (preferred halogens being fluorine and chlorine, as in, for example, trifluoromethyl), and R' represents alkyl, alkenyl or alkynyl, each with up to 4 carbon atoms, or phenyl, benzyl or styryl, the three last-mentioned radicals optionally carrying one or more substituents selected from halogen (especially fluorine, chlorine and bromine), cyano, nitro and halogenoalkyl with 1 or 2 carbon atoms and up to 3 identical or different halogen atoms (preferred halogens being fluorine and chlorine, as in, for example, trifluoromethyl).

Surprisingly, the 1-phenyl-2-triazolyl-ethyl ether derivatives according to the invention exhibit a substantially greater fungicidal activity, especially against species of rust and species of mildew, than the 1-[β-aryl-β-(alkoxy)-ethyl]-imidazoles known from the state of the art, for example 1-[β-butoxy-β-(4'-chlorophenyl)-ethyl]-imidazole, which, chemically and in respect of their action, represent the nearest compounds, and than zinc ethylene-1,2bis-dithiocarbamate, which is a known compound of the same type of action. The active compounds according to the invention thus represent an enrichment of the art.

The present invention also provides a process for the preparation of a 1-phenyl-2-triazolyl-ethyl ether derivative of the formula (I) in which an alkali metal alkanolate of a 1-hydroxy-1-phenyl-2-triazolyl-ethane derivative, of the general formula

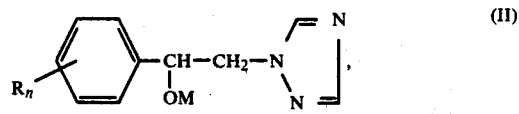

in which
R and n have the abovementioned meanings and
M represents an alkali metal, preferably lithium, sodium or potassium, is reacted with a halide of the general formula

in which
R' has the abovementioned meaning and
Hal represents halogen, preferably chlorine, bromine or iodine,
in the presence of a diluent.

If the sodium alkanolate of 1-hydroxy-1-(2',4'-dichlorophenyl)-2-(1,2,4-triazol-1-yl)-ethane and 2,4-dichlorobenzyl chloride are used as starting materials, the course of the reaction can be represented by the following equation:

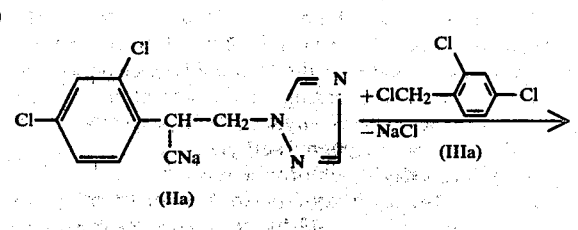

-continued

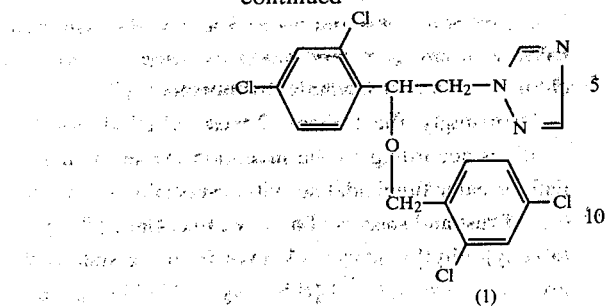

The alkali metal alkanolates of the formula (II) were not previously known. They are obtained by reacting the corresponding 1-hydroxy-1-phenyl-2-triazolyl-ethane derivatives with suitable strong bases, such as alkali metal amides or alkali metal hydrides, in an inert solvent.

The 1-hydroxy-1-phenyl-2-triazolyl-ethane derivatives mentioned above have also not been described previously. However, their preparation is described in U.S. Pat. application Ser. No. 792,756, filed May 2, 1977, now pending. They are obtained by reduction of the corresponding triazolylalkanones of the formula

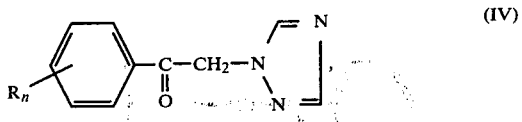

in which

R and n have the abovementioned meanings, by means of aluminum isopropylate, with formamidinesulfinic acid and alkali metal hydroxide or with complex hydrides as shown in the preparative examples hereinbelow.

The compounds of the formula (IV) are also new. Their preparation is also shown in the abovementioned patent application. The compounds are obtained, for example, by reacting halogenoketones of the formula

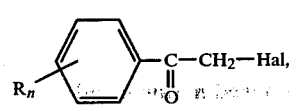

in which

R and n have the abovementioned meanings, and

Hal represents chlorine or bromine, with 1,2,4-triazoles in the presence of an acid-binding agent, as also shown in the preparative examples hereinbelow.

Halogenoketones of the formula (V) are disclosed in Bulletin de la Societe Chimique de France 1955, pages 1,363–1,383 and can be prepared in accordance with the processes described there, in U.S. Pat. No. 3,679,697 and German Published DOS No. 2,063,857.

The following may be mentioned as examples of the 1-hydroxy-1-phenyl-2-triazolyl-ethane derivatives from which the alkanolates of the formula (II), to be used as starting materials according to the invention, are derived: 1-(2-hydroxy-2-phenyl-ethyl)-1,2,4-triazole, 1-(2-hydroxy-2-(2'-methylphenyl)-ethyl)-1,2,4-triazole, 1-(2-hydroxy-2-(2'-ethyl-4'-chlorophenyl)-ethyl)-1,2,4-triazole, 1-(2-hydroxy-2-(4'-trifluoromethylphenyl)-ethyl)-1,2,4-triazole, 1-(2-hydroxy-2-(4'-nitrophenyl)-ethyl)-1,2,4-triazole, 1-(2-hydroxy-2-(2'-fluorophenyl)-ethyl)-1,2,4-triazole, 1-(2-hydroxy-2-(2'-chlorophenyl)-ethyl)-1,2,4-triazole, 1-(2-hydroxy-2-(2',4'-dichlorophenyl)-ethyl)-1,2,4-triazole, 1-(2-hydroxy-2-(4'-bromophenyl)-ethyl)-1,2,4-triazole, 1-(2-hydroxy-2-(3'-iodophenyl)-ethyl)-1,2,4-triazole, 1-(2-hydroxy-2-(4'-cyanophenyl)-ethyl)-1,2,4-triazole, 1-(2-hydroxy-2-(2'-methoxyphenyl)-ethyl)-1,2,4,-triazole, 1-(2-hydroxy-2-(2'-ethylthiophenyl)-ethyl)-1,2,4-triazole, 1-(2-hydroxy-2-(4'-methylsulfonylphenyl)-ethyl)-1,2,4-triazole, 1-(2-hydroxy-2-(2',4',5'-trichlorophenyl)-ethyl)-1,2,4-triazole, 1-(2-hydroxy-2-(4'-biphenylyl)-ethyl)-1,2,4-triazole, 1-(2-hydroxy-2-(4''-chloro-4'-biphenylyl)-ethyl)-1,2,4-triazole, 1-(2-hydroxy-2-(2'',4''-dichloro-4'-biphenylyl)-ethyl)-1,2,4-triazole, 1-(2-hydroxy-2-(2''-fluoro-2'-biphenylyl)-ethyl)-1,2,4-triazole, 1-(2-hydroxy-2-(4''-trifluoromethyl-4'-biphenylyl)-ethyl)-1,2,4-triazole, 1-(2-hydroxy-2-(4'-phenoxyphenyl)-ethyl)-1,2,4-triazole, 1-(2-hydroxy-2-[4'-(4''-chlorophenoxy)-phenyl]-ethyl)-1,2,4-triazole, 1-(2-hydroxy-2-[4'-(2'',4''-dichlorophenoxy)-phenyl]-ethyl)-1,2,4-triazole, 1-(2-hydroxy-2-[4'-(3''-nitrophenoxy)-phenyl]-ethyl)-1,2,4-triazole and 1-(2-hydroxy-2-[4'-(4''-bromophenoxy)-phenyl]-ethyl)-1,2,4-triazole.

The starting materials of the formula (III) are generally known compounds in organic chemistry. The following may be mentioned as examples: methyl chloride, ethyl bromide, n-propyl bromide, n-butyl bromide, t-butyl bromide, allyl bromide, allyl iodide, vinyl bromide, buten-2-yl chloride, propynyl chloride, chlorobenzene, p-dichlrorobenzene, p-dibromobenzene, o-dichlorobenzene, 1,2,4-dichlororomobenzene, 1,2,4-dichlorofluorobenzene, 1,2,4-trichlorobenzene, p-bromochlorobenzene, p-bromofluorobenzene, p-chlorofluorobenzene, p-chloroiodobenzene, p-chlorotrifluoromethylbenzene, 4-chlorobenzylchloride, 2,4-dichlorobenzyl bromide, 2,4-dichlorobenzyl iodide, 2,5-bromochlorobenzyl chloride, 2-nitrobenzyl chloride, 2-cyanobenzyl chloride, benzyl chloride, stryl chloride and 2,4-dichlorostyryl chloride.

Preferred salts of the compounds of the formula (I) are salts with physiologically tolerated acids, especially the hydrogen halide acids, such as, for example, hydrochloric acid and hydrobromic acid, phosphoric acid and nitric acid, as well as monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and finally sulfonic acids, such as 1,5-naphthalenedisulfonic acid.

The salts of the compounds of the formula (I) can be obtained in a simple manner in accordance with customary methods of forming salts, for example by dissolving the base in ether, for example diethyl ether, and adding the acid, for example hydrogen chloride, and can be isolated in a known manner, for example by filtration, and be purified if necessary.

Suitable diluents for the reaction according to the invention are inert organic solvents, especially ethers, such ad diethyl ether and dioxane, benzene, and, in some cases chlorinated hydrocarbons, such as chloroform, methylene chloride or carbon tetrachloride, and hexamethylphosphoric acid triamide.

The reaction temperatures can be varied within a fairly wide range. In general, the reaction is carried out at between 20° and 150° C., preferably at the boiling point of the solvent, for example at between 60° and 100° C.

In carrying out the process according to the invention, preferably 1 mole of halide of the formula (III) is employed per mole of the alkanolate of the formula (II). To isolate the end products, the reaction mixture is freed from the solvent, and water and an organic solvent are added to the residue. The organic phase is separated off, worked up in the usual manner, and purified; if desired, the salt may then be prepared.

According to a preferred embodiment, an advantageous procedure is to start from a 1-hydroxy-1-phenyl-2-triazolylethane derivative, convert the latter, in a suitable inert solvent, by means of an alkali metal hydride or alkali metal amide into the alkali metal alkanolate of the formula (II), and react the latter immediately, without isolation, with a halide of the formula (III), whereby the compounds according to the invention, of the formula (I), are obtained in one step, with elimination of alkali metal halide.

The active compounds according to the invention exhibit a powerful fungitoxic and bacteriotoxic action. They do not damage crop plants in the concentrations required for combating fungi and bacteria. For these reasons they are suitable for use as plant protection agents for combating fungi and bacteria. Fungitoxic agents are employed in plant protection for combating Plasmodiophoramycetes, Oomycetes, Chytridiomycetes, Zygomycetes, Ascomycetes, Basidiomycetes and Deuteromycetes.

The active compounds according to the invention have a broad spectrum of action and can be used against parasitic fungi which infest above-ground parts of plants or attack the plants through the soil, and against seed-borne pathogens.

They exhibit a particularly good activity against parasitic fungi on above-ground parts of plants, such as species of Erysiphe, species of Podosphaera and species of Venturia, for example against the pathogen of powdery mildew of apples (*Podosphaera leucotricha*) and of apple scab (*Fusicladium dendriticum*). They furthermore exhibit a high activity aganst cereal diseases, such as against powdery mildew of cereals and cereal rust.

In addition, the partially systemic action of the compounds should be pointed out. Thus it proves possible to protect plants against fungal attack by supplying the active compound to the above-ground parts of the plant through the soil and the root.

As plant protection agents, the active compounds according to the invention can be used for the treatment of seed and for the treatment of above-ground parts of plants. They have only a low toxicity to warm-blooded animals and, because of their low odor and their good toleration by human skin, they are not unpleasant to handle.

When used as seed dressings, the compounds according to the invention are active against seed-borne fungal diseases of plants, namely through disinfecting the surface of the seed, whereby, for example, they are active against stripe disease of barley, and also by systemic action against fungal pathogens in the interior of the seed, as in the case of loose smut of wheat and of barley. Furthermore, seed dressing results in a systemic protective action against fungal infections of the shoots, for example against mildew.

The active compounds according to the instant invention can be utilized, if desired, in the form of the usual formulations or compositions with conventional inert (i.e. plant-compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petoleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and bactericides, or nematocides, insecticides, acaricides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.00001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liter/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially in the case of use as leaf fungicides, the active compound concentrations in the use forms can be varied within a fairly wide range. They are in general from 0.1 to 0.00001 percent by weight, and preferably from 0.05 to 0.001 percent.

In the treatment of seed, amounts of active compound of 0.001 to 50 g per kilogram of seed, preferably 0.01 to 10 g, are in general required.

Furthermore, the present invention contemplates methods of selectively killing, combating or controlling pests, e.g. fungi and bacteria, and more particularly methods of combating fungi, which comprises applying to at least one of correspondingly (a) such fungi, (b) such bacteria, and (c) the corresponding habitat thereof, i.e. the locus to be protected, e.g. to a growing crop, to an area where a crop is to be grown or to a domestic animal, a correspondingly combative or toxic amount, i.e. a fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Erysiphe test (cucumbers)/protective
Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoriacearum*. The plants were subsequently placed in a greenhouse at 23°–24° C. and at a relative atmospheric humidity of about 75%.

After 12 days, the infection of the cucumber plants was determined.

0% means no infection; 100% means that the plants were completely infected.

The active compounds, the concentrations of the active compounds and the results can be seen from the following table:

TABLE 1

| | Erysiphe test (cucumbers)/protective | | |
|---|---|---|---|
| | | Infection in % at an active compound concentration of | |
| Active compound | 0.00062% | 0.0005% | 0.0001% |
| Cl—C$_6$H$_4$—CH(O—C$_4$H$_9$)—CH$_2$—N(pyrrole) × naphthalene-1,5-disulfonic acid (SO$_3$H) (Aa) | | 62 | |
| (known) | | | |

TABLE 1-continued

Erysiphe test
(cucumbers)/protective

| Active compound | Infection in % at an active compound concentration of | | |
|---|---|---|---|
| | 0.00062% | 0.0005% | 0.0001% |

[Structure (1): 2,4-dichlorophenyl-CH(O-CH2-2,4-dichlorophenyl)-CH2-N(triazole)] — 0

[Structure (2a): 2,4-dichlorophenyl-CH(O-CH2-CH=CH2)-CH2-N(triazole) × HNO3] — 4

[Structure (3): 2,4-dichlorophenyl-CH(O-CH2-C≡CH)-CH2-N(triazole) × HNO3] — 9

[Structure (4): 4-chlorophenyl-CH(O-CH2-2,4-dichlorophenyl)-CH2-N(triazole)] — 25

[Structure (5): 4-chlorophenyl-CH(O-CH2-4-chlorophenyl)-CH2-N(triazole)] — 2

[Structure (6): 2,4-dichlorophenyl-CH(O-CH2-2,6-dichlorophenyl)-CH2-N(triazole)] — 0

TABLE 1-continued

Erysiphe test
(cucumbers)/protective

| Active compound | Infection in % at an active compound concentration of | | |
|---|---|---|---|
| | 0.00062% | 0.0005% | 0.0001% |
| (7) | 59 | | |
| (1a) | 0 | | |
| (1b) | 0 | | |
| (4b) | 22 | | |
| (5a) | 6 | | |

TABLE 1-continued

Erysiphe test
(cucumbers)/protective

| Active compound | Infection in % at an active compound concentration of | | |
|---|---|---|---|
| | 0.00062% | 0.0005% | 0.0001% |
| (5b) | | | 0 |
| (6a) | | | 0 |
| (6b) | | | 0 |
| (7b) | | | 62 |
| | | | 0 |

TABLE 1-continued

Erysiphe test (cucumbers)/protective

| Active compound | Infection in % at an active compound concentration of | | |
|---|---|---|---|
| | 0.00062% | 0.0005% | 0.0001% |
| 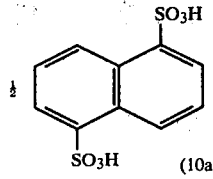 (10a) | | | |
| 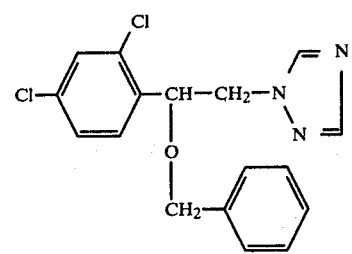 (comparison) | 91 | | |
| 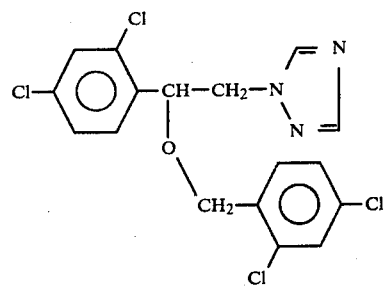 | 12 | | |
| 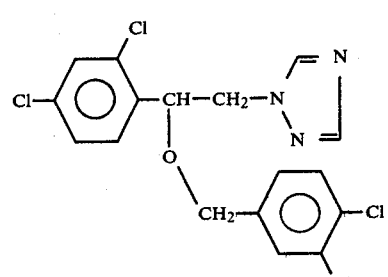 | 2 | | |

EXAMPLE 2

Fusicaladium test (apple scab)/Protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants were then brought into a greenhouse for 14 days.

15 days after inoculation, the infection of the seedlings is determined.

0% means no infection; 100% means that the plants are completely infected.

The active compounds, the concentrations of the active compounds and the results can be seen from the following table:

TABLE 2

Fusicladium test/protective

| Active compound | Infection in % at an active compound concentration of 0.00062% | 0.00025% |
|---|---|---|

Compound (Aa) (known): 4-chlorophenyl-CH(O-C₄H₉)-CH₂-N(triazole) — 59

Naphthalene-1,5-disulfonic acid (SO₃H groups at 1,5 positions)

Compound (1): 2,4-dichlorophenyl-CH[O-CH₂-(2,4-dichlorophenyl)]-CH₂-N(triazole) — 0

Compound (2a): 2,4-dichlorophenyl-CH(O-CH₂-CH=CH₂)-CH₂-N(triazole) × HNO₃ — 22

Compound (3): 2,4-dichlorophenyl-CH(O-CH₂-C≡CH)-CH₂-N(triazole) × HNO₃ — 35

Compound (4): 4-chlorophenyl-CH[O-CH₂-(2,4-dichlorophenyl)]-CH₂-N(triazole) — 2

TABLE 2-continued

Fusicladium test/protective

| Active compound | Infection in % at an active compound concentration of | |
|---|---|---|
| | 0.00062% | 0.00025% |
| (5) | | 9 |
| (6) | | 5 |
| (7) | | 2 |
| (1a) | — | 15 |
| (4a) | — | 34 |

TABLE 2-continued

Fusicladium test/protective

| Active compound | Infection in % at an active compound concentration of | |
|---|---|---|
| | 0.00062% | 0.00025% |
| (5a) Cl—C6H4—CH(O-CH2-C6H4-Cl)—CH2—N(triazole) × ½ naphthalene-1,5-disulfonic acid | | 40 |
| (7b) Cl—C6H4—CH(O-CH2-C6H3Cl2)—CH2—N(Cl-triazole) × HNO3 | | 48 |

EXAMPLE 3

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Drechslera graminea* (previously *Helminthosporium gramineum*), was shaken with the dressing in a closed glass flask. The seed, on moist filter paper discs in closed Petri dishes, was exposed to a temperature of 4° C. for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18° C. in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentrations of the active compounds in the dressing, the amounts of dressing used and the number of diseased plants can be seen from the following table:

TABLE 3

Seed dressing test/stripe disease of barley

| Active compound | Active compound concentration in the dressing in % by weight | Amount of dressing used in g/kg of seed | Number of plants with stripe disease, in % of the emerged plants |
|---|---|---|---|
| Without dressing | — | — | 60.6 |
| (known) (B) [CH2—NHCS(=S)]2Zn | 30 | 2 | 50.0 |
| (2a) Cl2-C6H3—CH(O-CH2-CH=CH2)—CH2—N(triazole) × HNO3 | 30 | 2 | 0.0 |

TABLE 3-continued
Seed dressing test/stripe disease of barley

| Active compound | Active compound concentration in the dressing in % by weight | Amount of dressing used in g/kg of seed | Number of plants with stripe disease, in % of the emerged plants |
| --- | --- | --- | --- |
| 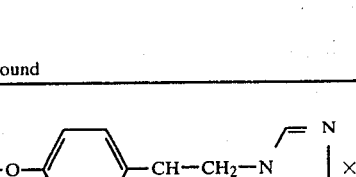 | 30 | 2 | 5.0 |

EXAMPLE 4

Powdery mildew of barley (*Erysiphe graminis* var. hordei)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. hordei and grown on at 21°–22° C., and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denotes no infection and 100% denotes the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

TABLE 4
Powdery mildew of barley test (*Erysiphe graminis* var. *hordei*)/systemic

| Active compounds | Active compound concentration in the dressing in % by weight | Amount of dressing used in g/kg of seed | Infection in % of the untreated control |
| --- | --- | --- | --- |
| Without dressing | — | — | 100.0 |
| 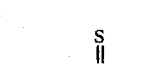 (known) (B) | 30 | 10 | 100.0 |
| 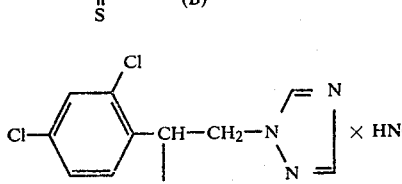 (3) | 30 | 10 | 0.0 |

TABLE 4-continued

Powdery mildew of barley test (*Erysiphe graminis* var. *hordei*)/systemic

| Active compounds | Active compound concentration in the dressing in % by weight | Amount of dressing used in g/kg of seed | Infection in % of the untreated control |
|---|---|---|---|
| 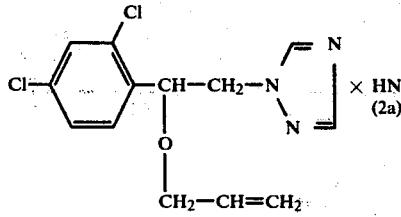 (2a) | 30 | 10 | 0.0 |
| 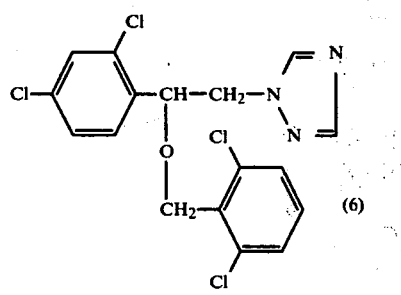 (6) | 30 | 10 | 0.0 |
| 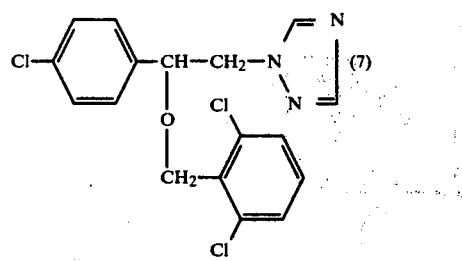 (7) | 30 | 10 | 0.0 |

EXAMPLE 5

Shoot treatment test/powdery mildew of cereals/-protective (leaf-destructive mycosis)

To produce a suitable preparation of active compound, 0.25 g part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test for protective activity, single-leaved young barley plants of the Amsel variety were sprayed with the preparation of active compound until dew-point. After drying, the young barley plants were dusted with spores of *Erysiphe graminis* var. *hordei*.

After 6 days' dwell time of the plants at a temperature of 21°–22° C. and 80–90% atmospheric humidity the occurrence of mildew pustules on the plants was evaluated. The degree of infection is expressed as a percentage of the infection of the untreated control plants. 0% denotes no infection and 100% denotes the same degree of infection as in the case of the untreated control. The more active the compound, the lower was the degree of mildew infection.

The active compounds, active compound concentrations in the spray liquor and degrees of infection can be seen from the table which follows:

TABLE 5

Shoot treatment test/powdery mildew of cereals/protective

| Active compounds | Active compound concentration in the spray liquor in % by weight | Infection in % of the untreated control |
|---|---|---|
| Untreated | — | 100.0 |
| 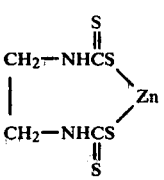 (known) (B) | 0.025 | 100.0 |

TABLE 5-continued
Shoot treatment test/powdery mildew of cereals/protective

| Active compounds | Active compound concentration in the spray liquor in % by weight | Infection in % of the untreated control |
|---|---|---|
| (6) 2,4-Cl-C6H3-CH(O-CH2-2,6-Cl2-C6H3)-CH2-N(triazole) | 0.025 | 0.0 |
| (7) 4-Cl-C6H4-CH(O-CH2-2,6-Cl2-C6H3)-CH2-N(triazole) | 0.025 | 0.0 |
| (5) 4-Cl-C6H4-CH(O-CH2-4-Cl-C6H4)-CH2-N(triazole) | 0.025 | 0.0 |
| (1b) 2,4-Cl2-C6H3-CH(O-CH2-3,4-Cl2-C6H3)-CH2-N(triazole) · HNO3 | 0.025 | 0.0 |
| (5b) 4-Cl-C6H4-CH(O-CH2-4-Cl-C6H4)-CH2-N(triazole) · HNO3 | 0.025 | 0.0 |
| (6b) 2,4-Cl2-C6H3-CH(O-CH2-2,6-Cl2-C6H3)-CH2-N(triazole) · HNO3 | 0.025 | 0.0 |
| 2,4-Cl2-C6H3-CH(O-CH2-C6H5)-CH2-N(triazole) (Comparison from DE-OS 2640 823) | 0.0025 | 58.8 |
| (1) 2,4-Cl2-C6H3-CH(O-CH2-(2,4-Cl2-cyclohexyl))-CH2-N(triazole) | 0.0025 | 0.0 |
| (12) (2-Cl-cyclohexyl)-CH(O-CH2-3,4-Cl2-C6H3)-CH2-N(triazole) | 0.0025 | 3.8 |

EXAMPLE 6

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denotes no infection and 100% denotes the same degree of infection as in the case of the untreated control. The more active the compound, the lower was the degree of rust infection.

The active compounds, active compound concentrations in the spray liquor and degrees of infection can be seen from the table which follows:

TABLE 6

Shoot treatment test/cereal rust/protective

| Active compounds | Active compound concentration in the spray liquor in % by weight | Infection in % of the untreated control |
|---|---|---|
| Untreated | — | 100.0 |
| CH₂—NHCS—Zn—CH₂—NHCS (S=) (known) (B) | 0.025 | 93.4 |
| Cl-C₆H₃(Cl)-CH(OCH₂-C₆H₃(Cl)(Cl))-CH₂-N(triazole) (1) | 0.025 | 0.0 |

EXAMPLE 7

Mycelium growth test
Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Composition of the solvent mixture:
  0.19 part by weight of dimethylformamide or acetone
  0.01 part by weight of emulsifier alkylaryl polyglycol ether
  1.80 parts by weight of water
Ratio of solvent mixture to nutrient medium:
  2 parts by weight of solvent mixture
  100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidifed, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:
  1 no fungus growth
  up to 3 very strong inhibition of growth
  up to 5 medium inhibition of growth
  up to 7 slight inhibition of growth
  9 growth equal to that of untreated control.

The active compounds, the active compound concentrations and the results can be seen from the following table:

TABLE 7

Mycelium growth test
Active compound concentration 10 ppm

| Active compound | Fungi | | | | | | | | | | | | |
|---|---|---|---|---|---|---|---|---|---|---|---|---|---|
| | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Sclerotinia sclerotiorum | Pellicularia sasakii |
| (1) | 5 | 5 | 2 | 1 | 3 | 3 | 5 | 2 | 1 | 1 | 3 | | |
| (2a) | | 5 | 3 | 2 | 5 | 1 | 1 | 1 | 1 | 1 | | | |
| (3) | | | | 5 | | 5 | 5 | 3 | 5 | 1 | | | |
| (4) | | | | | | 5 | 1 | 3 | 5 | 1 | 5 | | |

TABLE 7-continued

Mycelium growth test
Active compound concentration 10 ppm

| Active compound | Fungi | | | | | | | | | | | |
|---|---|---|---|---|---|---|---|---|---|---|---|---|
| | Colleto-trichum coffeanum | Rhizoc-tonia solani | Pythium ultimum | Cochlio-bolus miya-beanus | Botrytis cinerea | Verti-cillium alboa-trum | Pyricu-laria oryzae | Phialo-phora cinere-scens | Helmintho-sporium gramineum | Mycosphae-rella musicola | Phyto-phthora cactorum | Sclerotinia sclerotiorum | Pelli-cularia sasakii |
| (5) structure | 5 | 1 | 3 | 1 | | 5 | 5 | 3 | 5 | 1 | 5 | | |
| (7) structure | | | | | | 5 | 1 | 5 | 5 | 1 | 5 | | |
| (1a) structure | | | | 1 | | 3 | 1 | | 3 | 1 | | 3 | 1 |

TABLE 7-continued

Mycelium growth test
Active compound concentration 10 ppm

| Active compound | Fungi | | | | | | | | | | | | |
|---|---|---|---|---|---|---|---|---|---|---|---|---|---|
| | Colleto-trichum coffeanum | Rhizoc-tonia solani | Pythium ultimum | Cochlio-bolus miya-beanus | Botrytis cinerea | Verti-cillium alboa-trum | Pyricu-laria oryzae | Phialo-phora cinere-scens | Helmintho-sporium gramineum | Mycosphae-rella musicola | Phyto-phthora cactorum | Sclerotinia sclerotiorum | Pelli-cularia sasakii |
| (1b) | 5 | 3 | 3 | 2 | 3 | 3 | 1 | — | 1 | 1 | — | 3 | 2 |
| (5b) | 5 | 1 | 3 | 3 | 3 | 3 | 3 | — | 2 | 1 | — | 5 | 1 |
| (6b) | — | — | 3 | 5 | 3 | 1 | 1 | — | 1 | 1 | — | 5 | 3 |
| (9a) | — | — | 5 | 3 | 3 | 3 | 1 | — | 1 | 1 | — | 5 | 1 |

TABLE 7-continued

Mycelium growth test
Active compound concentration 10 ppm

| Active compound | Colleto-trichum coffeanum | Rhizoc-tonia solani | Pythium ultimum | Cochlio-bolus miya-beanus | Botrytis cinerea | Verti-cillium alboa-trum | Fungi Pyricu-laria oryzae | Phialo-phora cinere-scens | Helmintho-sporium gramineum | Mycosphae-rella musicola | Phyto-phthora cactorum | Sclerotinia sclerotiorum | Pelli-cularia sasakii |
|---|---|---|---|---|---|---|---|---|---|---|---|---|---|
| (11a) Cl—⟨C₆H₄⟩—O—⟨C₆H₄⟩—CH(O-CH₂-CH=CH₂)—CH₂—N(N=CH-N)  × ½ naphthalene-1,5-disulfonic acid (2 SO₃H) | 1 | 5 | 5 | 3 | — | 5 | 1 | — | 1 | 1 | — | 5 | 1 |

EXAMPLE 8

Uromyces test (bean rust)/protective
Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated additives.

Young bean plants, which were in the 2-leaved stage, were sprayed with the spray liquor until dripping wet. The plants remained in a greenhouse for 24 hours at 20°–22° C. and a relative atmospheric humidity of 70% in order to dry. They were then inoculated with an aqueous uredospore suspension of the causative organism of bean rust (Uromyces phaseoli) and incubated for 24 hours in a dark humidity chamber at 20°–22° C. and 100% relative atmospheric humidity.

The plants were then set up in a greenhouse under intensive illumination for 9 days at 20°–22° C. and a relative atmospheric humidity of 70–80%.

10 days after the inoculation, the infection of the plants was determined.

0% denotes no infection and 100% denotes that the plants are completely infected.

The active compounds, active compound concentrations and results can be seen from the following table:

TABLE 8

Uromyces test/protective

| Active compound | Infection in % at an active compound concentration of 0.01% |
|---|---|
| 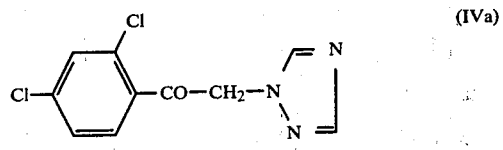 (known) (Aa) | 59 |
| (2a) | 41 |
| (3) | 50 |
| (4) | 46 |
| (5) | 41 |

The process of the present invention is illustrated by the following preparative examples:

EXAMPLE 9

(a) Preparation of the starting material

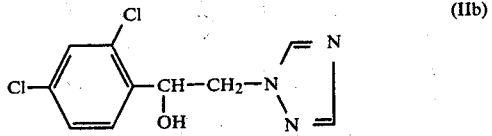 (IVa)

269 g (1 mole) of ω-bromo-2,4-dichloroacetophenone were dissolved in 250 ml of acetonitrile. This solution was added dropwise to a suspension, boiling under reflux, of 69 g (1 mole) of 1,2,4-triazole and 150 g of potassium carbonate in 2 l of acetonitrile. After heating for 20 hours under reflux, the suspension was allowed to cool and was filtered, the filtrate was freed from the solvent and the residue was taken up with ethyl acetate; this solution was washed with water, dried over sodium sulfate and freed from the solvent. The residue from the ethyl acetate crystallized out on adding isopropanol. After recrystallization from ligroin/isopropanol, 154 g (60% of theory) of ω-(1,2,4-triazol-1-yl)-2,4-dichloroacetophenone of melting point 117° C. were obtained.

(b) Preparation of the intermediate (IIb)

25.6 g (0.1 mole) of ω-(1,2,4-triazol-1-yl)-2,4-dichloroacetophenone were dissolved in 300 ml of methanol and 4 g (0.1 mole) of sodium borohydride were added in portions at 5° to 10° C., while stirring. The mixture was then stirred for a further hour at room temperature and heated to the boil for one hour. After distilling off the solvent, the residue was heated briefly with 200 ml of water and 40 ml of concentrated hydrochloric acid. After the reaction mixture had been rendered alkaline with sodium hydroxide solution, the solid reaction product could be filtered off. After recrystallization from ligroin/isopropanol, 21.3 g (82% of theory) of 1-hydroxy-1-(2',4'-dichlorophenyl)-2-(1,2,4-triazol-1-yl)-ethane of melting point 90° C. were obtained.

(c) 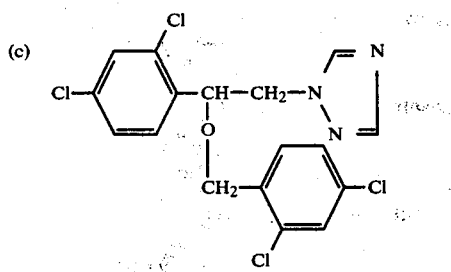 (1)

25.8 g (0.1 mole) of 1-hydroxy-1-(2',4'-dichlorophenyl)-2-(1,2,4-triazol-1-yl)-ethane were dissolved in 125 ml of dioxane and added dropwise, while stirring, to a mixture of 4 g of 80% strength sodium hydride and 100 ml of dioxane. The mixture was then heated under reflux for one hour. After cooling, 20 g (0.1 mole) of 2,4-dichlorobenzyl chloride were added dropwise, at room temperature, to the sodium salt obtained above. The mixture was then heated under reflux for several hours, was allowed to cool and was concentrated by distilling off the solvent. Water and methylene chloride were added to the residue and the organic phase was separated off, dried over sodium sulfate and concentrate. The solid residue was recrystallized from ligroin. 29 g (70% of theory) of 1-(2',4'-dichlorophenyl)-2-(1,2,4-triazol-1-yl)-ethyl 2',4'-dichlorobenzyl ether of melting point 84° C. were obtained.

EXAMPLE 10

(a) 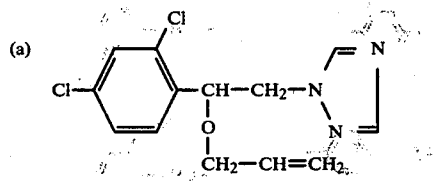 (2)

25.7 g (0.1 mole) of 1-hydroxy-1-(2',4'-dichlorophenyl)-2-(1,2,4-triazol-1-yl)-ethane were dissolved in 125 ml of dioxane and the solution was added dropwise, while stirring, to a suspension of 4 g of 80% strength sodium hydride in 150 ml of dioxane. The mixture was then heated under reflux for one hour. After it had cooled, 22.1 g (0.1 mole) of allyl bromide were added at room temperature to the sodium salt thus obtained. The mixture was then heated for 8 hours under reflux, was allowed to cool and was concentrated by distilling off the solvent. Water and methylene chloride were added to the residue and the organic phase was separated off, dried over sodium sulfate and concentrated. 29.5 g of 1-(2',4'-dichlorophenyl)-2-(1,2,4-triazol-1-yl)-ethyl allyl ether having a refractive index $n_D^{22}$ of 1.545 remained; this yield was practically quantitative.

(b) 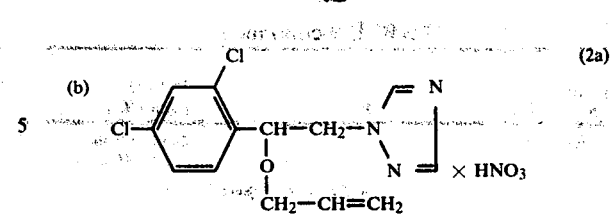 (2a)

29.5 g (0.1 mole) of 1-(2',4'-dichlorophenyl)-2-(1,2,4-triazol-1-yl)-ethyl allyl ether were dissolved in 200 ml of chloroform and 6.4 g of 95% strength nitric acid were added. The crystallization of the salt was completed by adding 250 ml of ether. After filtering off and drying, 34 g (95% of theory) of 1-(2',4'-dichlorophenyl)-2-(1,2,4-triazol-1-yl)-ethyl allyl ether nitrate of melting point 131° C. were obtained.

The following compounds of the general formula

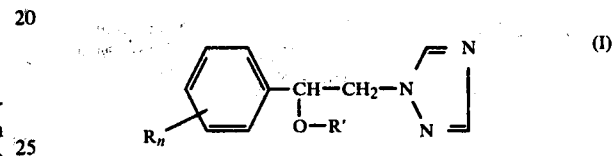 (I)

were prepared by procedures analogous to those of the above examples:

TABLE 9

| Compound No. | $R_n$ | R' | Melting point (°C.) |
|---|---|---|---|
| 3 | 2,4-Cl$_2$ | —CH$_2$—C≡CH | Nitrate 130 (decomposition) |
| 4 | 4-Cl | —CH$_2$—(3,4-Cl$_2$-phenyl) | 78 |
| 5 | 4-Cl | —CH$_2$—(4-Cl-phenyl) | 111 |
| 6 | 2,4-Cl$_2$ | —CH$_2$—(2,4-Cl$_2$-phenyl) | 120 |
| 7 | 4-Cl | —CH$_2$—(2,4-Cl$_2$-phenyl) | 118 |
| 8 | 4-Cl | —CH$_2$—CH=CH$_2$ | Naphthalene-1,5-disulfonate 225 (decomposition) |
| 1a | 2,4-Cl$_2$ | —CH$_2$—(2,4-Cl$_2$-phenyl) | Naphthalene-1,5-disulfonate 226 |
| 1b | 2,4-Cl$_2$ | —CH$_2$—(2,4-Cl$_2$-phenyl) | Nitrate 174 |

TABLE 9-continued

| Compound No. | $R_n$ | R' | Melting point (°C.) |
|---|---|---|---|
| 4a | 4-Cl | -CH$_2$-(2,4-Cl$_2$-phenyl) | Naphthalene-1,5-disulfonate 221 |
| 4b | 4-Cl | -CH$_2$-(2,4-Cl$_2$-phenyl) | Nitrate 148 |
| 5a | 4-Cl | -CH$_2$-(2-Cl-phenyl) | Naphthalene-1,5-disulfonate 229 |
| 5b | 4-Cl | -CH$_2$-(2-Cl-phenyl) | Nitrate 141 |
| 6a | 2,4-Cl$_2$ | -CH$_2$-(2,6-Cl$_2$-phenyl) | Naphthalene-1,5-disulfonate 273 |
| 6b | 2,4-Cl$_2$ | -CH$_2$-(2,6-Cl$_2$-phenyl) | Nitrate 194 |
| 7a | 4-Cl | -CH$_2$-(2,3-Cl$_2$-phenyl) | Naphthalene-1,5-disulfonate 250 |
| 7b | 4-Cl | -CH$_2$-(2,3-Cl$_2$-phenyl) | Nitrate 176 |
| 9a | 4-O-phenyl | -CH$_2$-CH=CH$_2$ | Naphthalene-1,5-disulfonate 184 |
| 10a | 4-O-(4-Cl-phenyl) | -CH$_2$-(2,4-Cl$_2$-phenyl) | Naphthalene-1,5-disulfonate 200 |
| 11a | 4-O-(4-Cl-phenyl) | -CH$_2$-CH=CH$_2$ | Naphthalene-1,5-disulfonate 213 |
| 12 | 2,4-di-Cl | -CH$_2$-(2,4-Cl$_2$-phenyl) | 89 |

Other compounds which can be similarly prepared include the following:

TABLE 10

| $R_n$ | R' |
|---|---|
| — | CH$_3$ |
| 2-CH$_3$ | C$_2$H$_5$ |
| 2-C$_2$H$_5$-4-Cl | n-C$_3$H$_7$ |
| 4-CF$_3$ | n-C$_4$H$_9$ |
| 4-NO$_2$ | t-C$_4$H$_9$ |
| 2-F | -CH=CH$_2$ |
| 2-Cl | -CH=CH-CH$_3$ |
| 4-Br | phenyl |
| 3-I | -(4-Cl-phenyl) |
| 4-CN | -(4-Br-phenyl) |
| 2-OCH$_3$ | -(2-Cl-phenyl) |
| 2-C$_2$H$_5$S- | -(2-Cl-4-Br-phenyl) |
| 4-CH$_3$SO$_2$- | -(2-Cl-4-F-phenyl) |
| 2,4,5-Cl$_3$ | -(2,4-Cl$_2$-phenyl) |
| 4-phenyl | -(4-F-phenyl) |
| 4-Cl-phenyl | -(4-I-phenyl) |
| 4-Cl-(2-Cl-phenyl) | -(4-CF$_3$-phenyl) |
| 2-(2-F-4-methylphenyl) | -CH$_2$-(2-Br-5-Cl-phenyl) |
| 4-CF$_3$-phenyl | -CH$_2$-(2-NO$_2$-phenyl) |
| 4-phenyl-O | -CH$_2$-(2-CN-phenyl) |
| 4-Cl-phenyl-O | -CH$_2$-phenyl |
| 4-Cl-(2-Cl-phenyl)-O- | -CH=CH-phenyl |
| 4-(2-NO$_2$-phenyl)-O- | -CH=CH-(2,4-Cl$_2$-phenyl) |

TABLE 10-continued

| $R_n$ | R' |
|---|---|
| 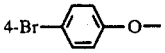 | —CH₃ | and the like, as well as salts thereof.

It will be appreciated that the instant specification and examples are set forth by way of illustration and not limitation, and that various modifications and changes may be made without departing from the spirit and scope of the present invention.

What we claim is:

1. A 1-chlorophenyl-2-(1,2,4-triazol-1-yl)-ethyl chlorobenzyl ether of the formula

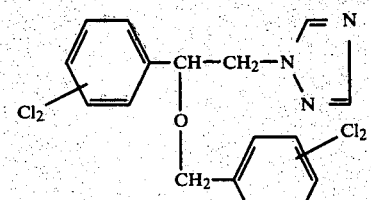

or a salt thereof with a physiologically tolerated acid.

2. A compound or salt thereof according to claim 1, wherein such compound is 1-(2',4'-dichlorophenyl)-2-(1,2,4-triazol-1-yl)-ethyl 2,4-dichlorobenzyl ether of the formula

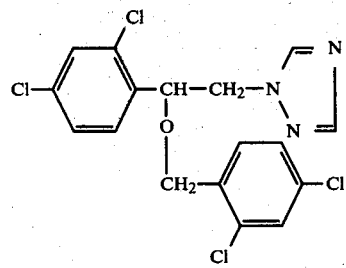

or a salt thereof with a physiologically tolerated acid.

3. A fungicidal composition comprising a fungicidally effective amount of a compound or salt according to claim 1 in admixture with a diluent.

4. A method of combating fungi which comprises applying to such fungi or a fungus habitat a fungicidally effective amount of a compound or salt according to claim 1.

* * * * *